US006303371B1

(12) United States Patent
Wadsworth

(10) Patent No.: US 6,303,371 B1
(45) Date of Patent: Oct. 16, 2001

(54) METHOD OF PURIFIED RAAV VECTOR PRODUCTION IN NON-HUMAN CELL LINE TRANSFECTED WITH COCKSACKIE AND ADENOVIRUS RECEPTOR

(75) Inventor: Samuel C. Wadsworth, Shrewsbury, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/601,099

(22) PCT Filed: Feb. 17, 1999

(86) PCT No.: PCT/US99/03482

§ 371 Date: Jul. 25, 2000

§ 102(e) Date: Jul. 25, 2000

(87) PCT Pub. No.: WO99/41399

PCT Pub. Date: Aug. 19, 1999

Related U.S. Application Data

(60) Provisional application No. 60/074,762, filed on Feb. 17, 1998.

(51) Int. Cl.$^7$ .......................... C12N 15/06; C12N 15/41; C12Q 1/70; A61K 48/00; A01N 1/01
(52) U.S. Cl. ....................... 435/320.1; 435/457; 435/465; 435/326; 435/339; 435/364; 435/352; 435/69.1; 435/325; 435/348; 536/23.1; 536/23.72; 536/24.1
(58) Field of Search .............................. 435/364, 320.1, 435/91.32, 457, 465, 326, 339, 69.1, 352, 325, 366, 367, 369, 348; 535/23.1, 23.72, 24.1

(56) References Cited

FOREIGN PATENT DOCUMENTS

| WO 96/13598 | 5/1996 | (WO) . |
| WO 96/22378 | 7/1996 | (WO) . |
| WO 97/09441 | 3/1997 | (WO) . |

OTHER PUBLICATIONS

Ross et al. J. Virol. 1992, vol. 66, pp. 3110–3117.*
Verma et al. Nature 1997, vol. 389, pp. 239–242.*
Orkin et al. 1996 Report and Recommendations of the Panel to Assess the NIH Investment in Research on Gene Therapy.*
"Avigen Reports In Vivo Delivery and Long Term Expression of Factor VIII Gene for Hemophilia A" (Nov. 1, 1999 Avigen Press Release).
"Researchers Describe Therapeutic Efficacy of Gene Therapy for Hemophilia B at American Society of Hematology Meeting" (Dec. 6, 1998 Avigen Press Release).
"Success of Gene Therapy Research for Canine Hemophilia B Shows Promise for Treating Humans" (Jan. 3, 1999 Avigen Press Release).
"Successful Hemophilia B Gene Therapy in Dogs" (Jan. 9, 1999 Science Daily News Release).
"Avigen Reports First Promising Human Gene Therapy Trial Results for Hemophilia B" (Dec. 6, 1999 Avigen Press Release).
"Avigen Researchers Report Safety and Gene Expression in Hemophilia B Gene Therapy Study" (Jun. 1, 2000 Avigen Press Release).
"Avigen Demonstrates Gene Therapy Success in Treating Animal Model of Parkinson's Disease" (Oct. 27, 1997 Avigen Press Release).
"Avigen's Gene Therapy Technology Shows Promise for Treating Parkinson's Disease" (Jun. 14, 1999 Avigen Press Release).
"Success with Erythropoietin" (Nov. 26, 1999 Avigen Press Release).
"Ribozyme, Chiron, City of Hope and Children's Hospital Announce Completion of Phase I/IIA HIV Gene Therapy Study" (Jan. 8, 1997 Chiron Press Release).
"Chiron and Green Cross Broaden Clinical Trials of Gene Therapy–Based HIV Immunotherapeutic" (Feb. 13, 1996 Chiron Press Releases).
"Gene Therapy Restores Two Babies" (Apr. 28, 2000, www.uphere.com News Release).
"Gene Therapy Proves Successful for Two Children" (Oct. 20, 1995, www.cnn.com News Release).
"Schering–Plough Reports Findings of p53 Gene Therapy Studies at Conference on Gene Therapy of Cancer Annual Meeting" (Nov. 23, 1998, Schering–Plough Press Release).
"Schering–Plough Presents Findings of p53 Gene Therapy Studies at American Association for Cancer Research Annual Meeting" (Mar. 31, 1998, Schering–Plough Press Release).
"Schering–Plough Reports on Clinical Progress of p53 Gene Therapy at Annual Gene Therapy of Cancer Meeting" (Nov. 20, 1997, Schering–Plough Press Release).
Flotte et al., "Expression of the Cystic Fibrosis Transmembrane Conductance Regulator from a Novel Adeno–associated Virus Promoter" J. of Biological Chem., 265 (5): 3781–9 (1993).
Flotte et al., "Stable in vivo expression of the cystic fibrosis transmembrane conductance regulator with an adeno–associated virus vector" Proc Natl Acad Sci USA, 90 (22): 10613–7 (1993).

(List continued on next page.)

Primary Examiner—James Housel
Assistant Examiner—Bao Qun Li
(74) Attorney, Agent, or Firm—Genzyme Corporation

(57) ABSTRACT

The invention is directed to novel systems for the high level production of purified recombinant adeno-associated virus (rAAV) vector stocks comprising producer cell lines and helper adenoviruses. These systems provide high level production of rAAV vector stocks that are not contaminated by helper viruses or have very minimal contamination with helper virus. The invention is also directed to methods for the production of high yield, purified rAAV vector stocks using the systems of the invention.

14 Claims, 4 Drawing Sheets

OTHER PUBLICATIONS

Flotte et al., "Adeno–associated virus vectors for gene therapy" Gene Therapy, 2 357–362 (1995).

Conrad et al., "Safety of single–dose administration of an adeno–associated viurs (AAV)–CFTR vector in the primate lung" Gene Therapy, 3, (8): 658–668 (1996).

Dong et al., "Quantitative Analysis of the Packaging Capacity of Recombinant Adeno–Associated Virus" Human Gene Therapy, 7: 2101–2112, (1996).

Rubenstein et al., CFTR gene transduction in neonatal rabbits using an adeno–associated virus (AAV) vector Gene Therapy, 4 (5): 384–392 (1997).

Ensinger et al., "Selection and Preliminary Characterization of Temperature–Sensitive Mutants of Type 5 Adenovirus" Journal of Virology, 10:328–339, (1972).

* cited by examiner

US 6,303,371 B1

METHOD OF PURIFIED RAAV VECTOR PRODUCTION IN NON-HUMAN CELL LINE TRANSFECTED WITH COCKSACKIE AND ADENOVIRUS RECEPTOR

This application is a 371 of PCT/US 99/03482, filed Feb. 17, 1999, which claims the benefit of U.S. Provisional Application No. 60/074,762 filed Feb. 17, 1998.

INTRODUCTION

The invention is directed to novel systems for the high level production of purified recombinant adeno-associated virus (rAAV) vector stocks comprising producer cell lines and helper adenoviruses. These systems provide high level production of rAAV vector stocks that are not contaminated by helper viruses or have very minimal contamination with helper virus. The invention is also directed to methods for the production of high yield, purified rAAV vector stocks using the systems of the invention.

BACKGROUND OF THE INVENTION

Adeno-associated virus (AAV) is a single-stranded human DNA parvovirus whose genome has a size about of 4.6 kb. The AAV genome contains two major genes: the rep gene, which codes for the rep proteins (Rep 76, Rep 68, Rep 52 and Rep 40) and the cap gene, which codes for AAV structural proteins (VP-1, VP-2 and VP-3). The rep proteins are involved in AAV replication, rescue, transcription and integration, while the cap proteins form the AAV viral particle. AAV derives its name from its dependence on an adenovirus or other helper virus (e.g., herpesvirus) to supply essential gene products that allow AAV to undergo a productive infection, i.e., reproduce itself in a host cell. In the absence of helper virus, AAV integrates as a provirus into a host cell's chromosome, until it is rescued by superinfection of the host cell with a helper virus, usually adenovirus (Muzyczka, Curr. Top. Micro. Immunol. 158:97–127, 1992).

Interest in AAV as a gene transfer vector (recombinant AAV, rAAV) results from several unique features of its biology. At both ends of the AAV genome is a nucleotide sequence known as an inverted terminal repeat (ITR), which contains cis-acting nucleotide sequences required for virus replication, rescue, packaging and integration. The integration function of the ITR, mediated by AAV rep proteins in trans, permits the AAV genome to integrate into a cellular chromosome after infection, in the absence of helper virus. This unique property of the virus has relevance to the use of rAAV in gene transfer, since it allows for the integration of a recombinant AAV containing a foreign nucleic acid (transgene) into the cellular genome. Therefore, stable genetic transformation, a major goal of gene transfer, may be achieved by use of rAAV vectors. Furthermore, the site of integration for AAV is well-established and has been localized to chromosome 19 of humans (Kotin et al., Proc. Natl. Acad. Sci. USA 87:2211–2215, 1990). This predictability of integration site reduces the danger of random insertional events into the cellular genome that may activate or inactivate host genes or interrupt coding sequences, consequences that can limit the use of vectors whose integration is random, e.g., retroviruses. However, because the rep proteins mediate the integration of AAV, removal of the rep gene in the design of rAAV vectors may result in the altered cellular integration patterns that have been observed with rAAV vectors (Ponnazhagan et al., Hum. Gene Ther. 8:275–284, 1997).

There are additional advantages to the use of AAV for gene transfer. The host range of AAV is broad. Moreover, unlike retroviruses, AAV can infect both quiescent and dividing cells. In addition, AAV has not been associated with human disease, obviating many of the concerns that have been raised with retrovirus-derived gene transfer vectors.

Progress in the development of AAV as a gene transfer vector, however, has been limited by an inability to produce high titer rAAV stocks. Standard approaches to the generation of rAAV vectors have required the coordination of a series of intracellular events: transfection of a host cell with an rAAV vector genome containing a transgene of interest flanked by the AAV ITR sequences, transfection of the host cell by a plasmid encoding the AAV rep gene whose protein products are required in trans, and infection of the transfected cell with a helper virus to supply the non-AAV helper functions required in trans (Muzyczka, N., Curr. Top. Micro. Immunol. 158: 97–129, 1992). The adenoviras (or other helper virus) proteins activate transcription of the AAV rep gene, and the rep protein products thereof then activate transcription of the AAV cap gene. The cap proteins then utilize the ITR sequences to package the rAAV genome into a virus particle.

The efficiency of packaging is determined, in part, by the availability of adequate amounts of the structural proteins (VP-1, VP-2, VP-3), as well as by the accessibility of any cis-acting packaging sequences required in the rAAV vector genome.

One of the potential limitations to high level rAAV production derives from limiting quantities of the AAV helper proteins (those encoded by the AAV rep and cap genes) required in trans for replication and packaging of the rAAV genome. Various approaches to increasing the levels of these proteins have included placing the AAV rep gene under the control of the HIV LTR promoter to increase the levels of rep proteins produced (Flotte, F. R. et al., Gene Therapy 2:29–37, 1995); the use of other heterologous promoters to increase production of the AAV helper proteins, specifically the cap proteins (Vincent et al., J. Virol. 71:1897–1905, 1997); and the development of cell lines containing the AAV rep gene that specifically produce the rep proteins (Yang, Q. et al., J. Virol. 68: 4847–4856, 1994).

Other approaches to improving the production of rAAV vectors include the use of helper virus induction of the AAV helper proteins (Clark et al., Gene Therapy 3:1124–1132, 1996) and the generation of a cell line containing integrated copies of the rAAV vector and AAV helper genes such that infection by the helper virus initiates rAAV production (Clark et al., Human Gene Therapy 6:1329–1341, 1995).

rAAV vectors have also been produced using either replication-defective helper adenoviruses which contain within their genome nucleotide sequences encoding a rAAV vector genome (U.S. Pat. No. 5,856,152 issued Jan. 5, 1999) or helper adenoviruses whose genomes contain nucleotide sequences encoding AAV helper proteins (PCT International Publication WO95/06743, published Mar. 9, 1995). Production strategies which combine high level expression of the AAV helper genes and the optimal choice of cis-acting nucleotide sequences inserted into a rAAV vector genome have been described (PCT International Application No. WO97/09441 published Mar. 13, 1997).

A further limitation to the production of high titer, purified rAAV stocks is that the requirement for the presence of a non-AAV helper virus can can lead to contamination of a vector stock preparation with helper virus. The helper virus can itself replicate during rAAV production, thereby requiring further technical manipulations of a cell lysate in order to produce a purified stock of rAAV vectors. In addition to the inefficiency in such purification techniques, the contamination by helper viruses is ultimately undesirable for therapeutic applications of rAAV as gene transfer vectors. Current approaches to reducing contamination of rAAV vector stocks by helper viruses, include, inter alia, the use of temperature-sensitive helper adenoviruses (Ensinger et al., J. Virol. 10:328–339, 1972), which are inactivated at the non-permissive temperature, used for producing rAAV stocks. Alternatively, the non-AAV helper genes can be subcloned into DNA plasmids which are transfected into a cell during rAAV vector production (Salvetti et al., Hum. Gene Ther. 9:695–706, 1998; Grimm et al., Hum. Gene Ther. 9:2745–2760, 1998).

The development of further rAAV production methods, which eliminate or reduce the replication of helper virus in the production of vector stocks and allow the generation of purified vector preparations, increases the feasibility of using rAAV for gene transfer. The present invention provides such methods.

SUMMARY OF THE INVENTION

The invention is directed to novel systems for the high level production of purified recombinant adeno-associated virus (rAAV) vector stocks comprising producer cell lines and helper adenoviruses. These systems provide high level production of rAAV vector stocks that are not contaminated by helper viruses or have very de minimis contamination with helper virus. The invention is also directed to methods for the production of high levels of purified rAAV vector stocks using of the invention.

DETAILED DESCRIPTION OF THE INVENTION

Figure 1:
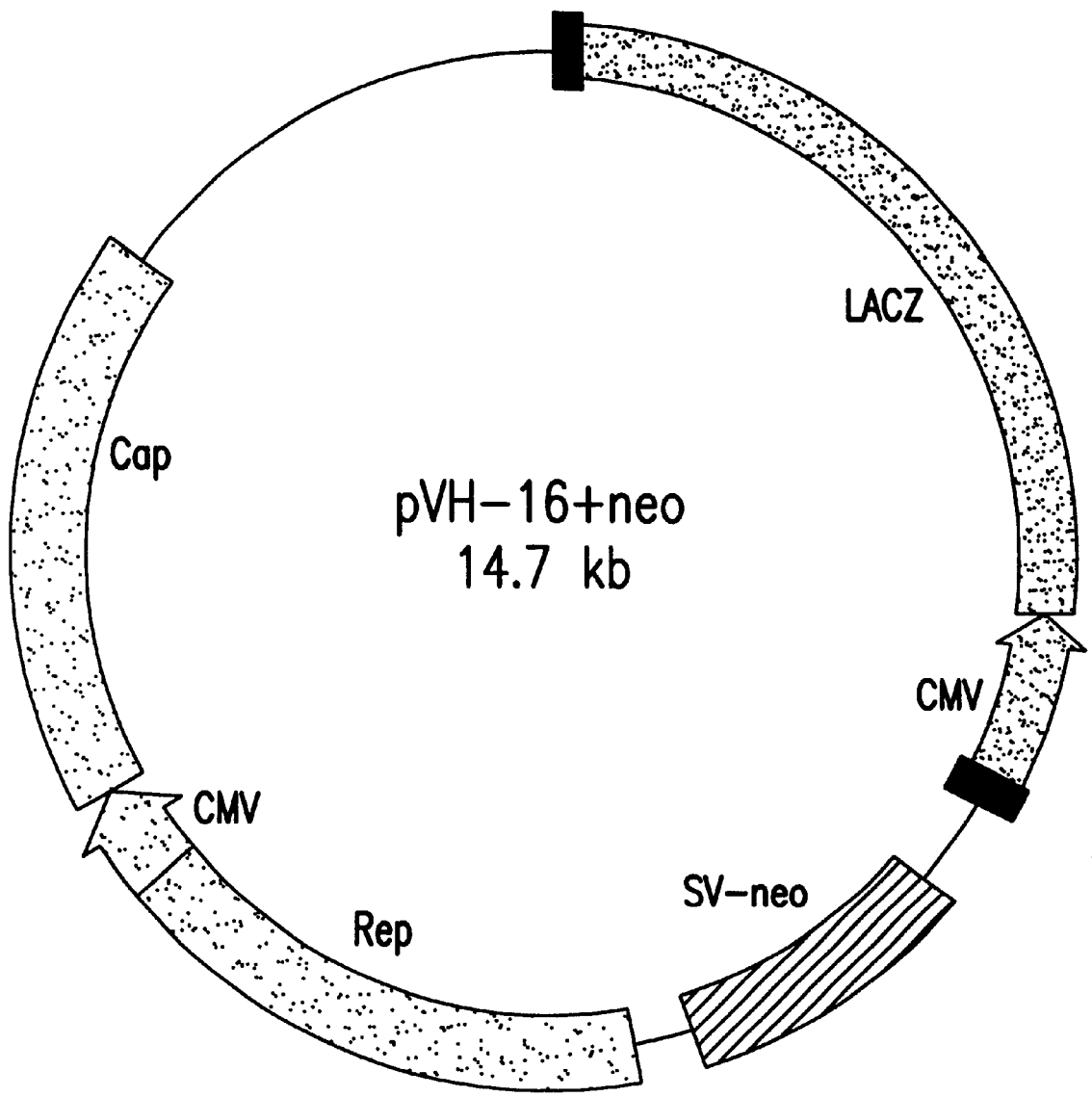
FIG. 1 shows a schematic diagram of plasmid pVH-16+neo.

The invention is directed to novel AAV vector production systems for the high level production of purified recombinant adeno-associated virus (rAAV) vector stocks comprising producer cell lines and helper adenoviruses. The systems of the invention support high level production of rAAV vectors with de minimis or no contamination by the helper viruses. The helper adenoviruses of the invention are characterized by an inability to generate a productive infection in a producer cell line. The producer cell lines of the invention are characterized by their inability to support a productive infection by human helper adenoviruses, a feature which enables high level production of purified rAAV vector stocks.

A helper virus is any non-AAV virus which provides gene products, e.g. proteins, required in trans for the replication and assembly of AAV into viral particles. In the absence of a helper virus, an AAV genome introduced into a host cell integrates and remains latent until superinfection of the host cell by a helper virus, which rescues the AAV viral genome and initiates a productive cycle of infection. The use of any helper virus which provides the non-AAV gene products, e.g. proteins, required in trans for rAAV production, but which is incapable of productive infection in a cell line of the invention, is within the scope of the invention. In the most preferred embodiment of the invention, the helper virus is adenovirus, whether wild-type or recombinant. The helper viruses of the invention are those which do not generate a productive infection in the producer cell line, but which enter the producer cell by infection using an endogenous virus receptor or an exogenously engineered receptor on surface of the producer cell.

The producer cell lines of the invention include (1) those which are not natively within the host range of the infecting helper virus and do not support a productive infection thereof, but which can be engineered to express a nucleic acid encoding a receptor that allows binding and entry thereto of the helper virus so that it can enter the cell in order to supply the gene products products, e.g. proteins, required in trans for rAAV production, or (2) those which are natively susceptible to binding and entry thereto by a helper virus, but will not support a productive infection by such virus.

The novel producer cell lines of the invention under (1) above are adapted to be susceptible to binding and entry of a helper virus required for the production of rAAV vectors, but are not capable of supporting a productive infection by the helper virus. With either class of cell line described above (1) or (2), production of an rAAV vector stock occurs with de minimis or no contamination by helper virus, thereby simplifying the preparation of a purified vector stock. In a preferred embodiment of the invention, the helper virus is a human adenovirus and the producer cell line is of non-human origin.

Preferably, producer cell lines of the invention for rAAV production are derived from mouse, hamster, rat, or monkey tissues, which are not natively susceptible to productive infection by human adenoviruses, but which are adapted to be susceptible to binding and entry by a human helper adenovirus. Such non-human cell lines are defined as "adapted" when they comprise a nucleic acid encoding a receptor for a human adenovirus which, upon expression, render such cells susceptible to human adenovirus binding and entry. However, such adaptation of the surface characteristics of the producer cells does not remove the barrier to productive infection by the helper adenovirus, which cannot replicate therein.

In order to render cells adapted to the binding and entry of the helper virus, thereby creating the producer cell lines of the invention, a nucleic acid encoding a specific receptor for a desired helper virus, e.g. adenovirus can be stably introduced into a cell line lacking such a receptor. The human adenovirus receptor has been characterized and identified as the cocksackie and adenovirus receptor (CAR). The gene (nucleic acid) coding for CAR has been sequenced (Bergelson et al., Science 275:1320–1323, 1997, incorporated herein by reference) and has been localized to human chromosome 21 (Mayr et al., J. Virol. 71:412–418, 1997). A non-human producer cell line which expresses the nucleic acid encoding CAR may be constructed using standard techniques of molecular biology and is within the scope of the present invention. The successful adaptation of mouse A9 cells to human adenovirus-binding capability has been demonstrated by providing human chromosome 21 to these cells which lack such a receptor for human adenovirus (Mayr et al., J. Virol. 71:412–418, 1997).

The human adenovirus receptor (CAR) is provided to a cell line lacking or deficient in such a receptor by transfection of the cells with a nucleic acid encoding the receptor or by transfection with a plasmid comprising the nucleic acid encoding the receptor by transfection with a large segment of human chromosome 21. Such plasmid or nucleic acid can also comprise a nucleic acid can also encoding a selectable marker, for example, the hygromycin resistance gene, which allows for the selection of transfected cells in the presence of hygromycin B. Such plasmids, nucleic acids or chromosome segment can also be introduced into the cells by any means of nucleic acid transfer, including, but not limited to, transfection, lipofection, electroporation, for example, or by vector-mediated delivery. Alternatively, a nucleic acid encoding CAR (Bergelson et al., Science 275:1320–1323, 1997) can also be supplied to a cell on a bacterial artificial chromosome (BAC). For example, Genome Systems (St. Louis, Mo.) or Research Genetics (Huntsville, Ala.) can insert desired nucleic acids, such as the nucleic acid encoding CAR, into recipient cells using BACs. Where the CAR encoding nucleic acid is provided to a recipient cell using a BAC, the CAR gene is expressed from its own promoter. When a nucleic acid encoding CAR is provided as a cDNA or a defined genomic fragment, the phosphoglycerate kinase (PGK) promoter is preferably used to drive expression thereof (Armentano et al., Hum. Gene Ther. 6:1343–1353, 1995). Provision of a nucleic acid encoding a human adenovirus receptor operably linked to such expression control sequences to recipient cells renders such cells susceptible to binding and entry of a human adenovirus.

Specific cell lines which can be adapted to express a nucleic acid encoding a human adenovirus receptor (and, therefore, be susceptible to human adenovirus binding and entry) and used to produce an rAAV stock with minimal contamination from a helper human adenovirus include, inter alia, mouse A9, mouse L929, Chinese hamster ovary (CHO), all of which are cell lines known to those skilled in the art.

The non-AAV helper virus that is required for rAAV vector production in the cell lines of the invention can be any non-AAV helper virus which provides expression of genes encoding non-AAV viral proteins required in trans for AAV replication and packaging. The helper virus is capable of binding and entering the producer cell line, but cannot generate a productive infection. Such helper viruses, include, but are not limited to, adenovirus, herpes simplex viruses I and II, vaccinia, cytomegalovirus and pseudorabies virus (Berns, K., "Parvoviridae: The Viruses and Their Replication" in Virology, Fields et al., eds., Lippincott-Raven, New York 1996). Chimeric helper viruses, which supply the required proteins in trans from more than one helper virus or more than one viral serotype, are also within the scope of the invention. A producer cell line of the invention which is adapted for the binding and entry of a helper virus can be customized according to the invention by the selection of a receptor protein which specifically allows the entry of the desired helper virus (e.g., adenovirus-CAR).

Preferably, the helper virus is a human adenovirus which is used in a producer cell line that cannot support productive infection by such viruses. The adenovirus helper virus or adenoviral genes used to produce an rAAV vector stock can be derived from any adenoviral serotype, including, but not limited to, those from group C, preferably serotypes 2 and 5. Adenovirus genes required for helper function include, inter alia, E1A, E1B, E2A, E40RF6, and VA RNA (Muzycka, N., Curr.Top.Micro.Immunol. 158:97–129, 1992). The adenovirus that can be used in rAAV vector production in the cell lines of the invention can be any wild-type or recombinant virus which provides expression of the adenovirus genes encoding proteins required in AAV replication. Alternatively, the adenovirus genes encoding the proteins required for AAV replication can be provided to a cell line of the invention in any mutant or truncated adenovirus, or can be provided on a plasmid by naked DNA.

Where the helper virus is a human adenovirus, non-human cell lines adapted as described above to bind the human adenoviruses by transfection with a nucleic acid encoding the appropriate receptor can be assayed for receptor function by the binding of radiolabelled human adenovirus, by using antibodies specific for the receptor which can be detected by standard signal detection, or by the ability of the transfected cells to bind the human adenovirus fiber protein, all of which are techniques known to those skilled in the art. Such techniques are also applicable to cells which have been adapted for the entry of other helper viruses, such as herpes simplex, etc.

In a preferred embodiment of the invention, an adapted producer cell line of the invention comprises a nucleic acid encoding the rAAV vector (and transgene), as well as AAV helper genes stably integrated into its genome. Upon infection of the cell line with a helper virus, rAAV production occurs because the rAAV genome is rescued and packaged, but the helper virus does not generate a productive infection. This method requires only the infection of the adapted producer cell line by the helper virus to generate an rAAV stock.

Alternatively, the nucleic acid encoding the rAAV vector sequences may be stably integrated into the producer cell genome and the AAV helper genes may be exogenously delivered to the cell, or the AAV helper genes may be stably integrated into the producer cell genome and the nucleic acid encoding the rAAV vector may be delivered exogenously to the cell. Further embodiments of the invention include the exogenous delivery of either the nucleic acid encoding the rAAV vector or the AAV helper genes in the form of a plasmid or by first inserting the vector and/or helper genes into a helper virus such as a recombinant adenovirus (containing a heterologous nucleic acid comprising the rAAV genome) or a herpesvirus and infecting the producer cell with such virus.

The invention is also directed to a novel rAAV producer system comprising a producer cell line derived from monkey cells and a helper human adenovirus. The helper virus is able to bind to and enter the producer cells but is unable to generate a productive infection therein, resulting in de minimis contamination of the rAAV vector stock by the helper virus. This system takes advantage of the finding that human adenoviruses undergo abortive infection in monkey cells (Anderson et al., Proc. Natl. Acad. Sci. USA 81:4034–4027, 1984; Ross et al., J. Virol. 66:3110–3117, 1992). However, the early genes of the helper adenovirus are expressed, thereby providing the essential adenoviral proteins required for rAAV production. The poor expression of adenoviral late genes in cells of monkey origin depresses the yield of adenovirus progeny, as well as reducing the the number of adenovirus proteins in the cell lysate, thereby simplifying the subsequent purification of the rAAV vectors. Preferred monkey cell lines for this production system include, but are not limited to, CV-1, CV-C (Rice et al., J. Virol. 49:35–49, 1984), Vero and BSC-1.

Figure 2:
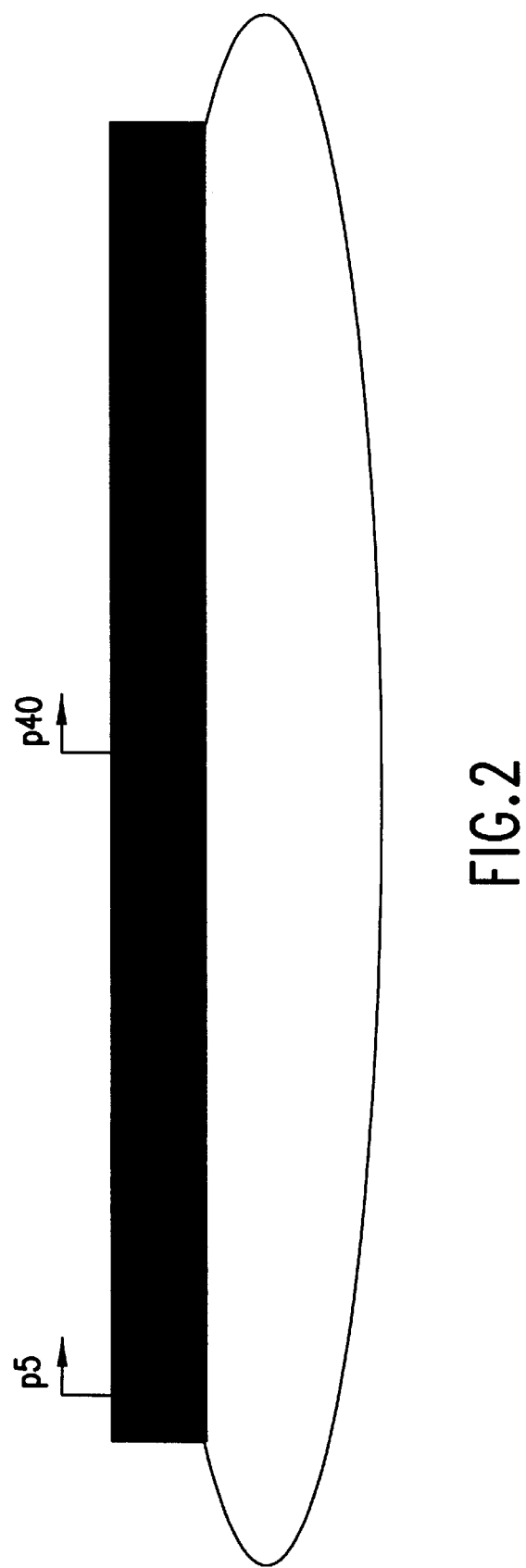
FIG. 2 shows a schematic diagram of AAV helper genes for insertion into a producer cell line.

Preferably, the monkey producer cell line comprises the AAV rep and cap genes under the control of native promoters (p5/rep and p40/cap) in order that the proteins encoded by these genes are directly provided by the producer cell. A schematic diagram of a construct containing the rep and cap genes under the control of these promoters and which is used to create these producer cells is shown in FIG. 2.

The invention is further directed to a novel adenovirus/rAAV hybrid vector which can be used to produce an rAAV vector stock. The hybrid vector supplies all essential adenovirus coding sequences and further contains an rAAV genome comprising a transgene operably linked to expression control elements and flanked by the AAV ITR sequences. A replication-competent embodiment of such a vector can be constructed by incorporating a rAAV genome into a region of the adenovirus genome which is not essential for replication, such as the E3 region. Where it is desirable to create a replication-defective hybrid vector, such a vector may include a rAAV genome in a deletion within, for example, the adenovirus E1 region.

Figure 3:
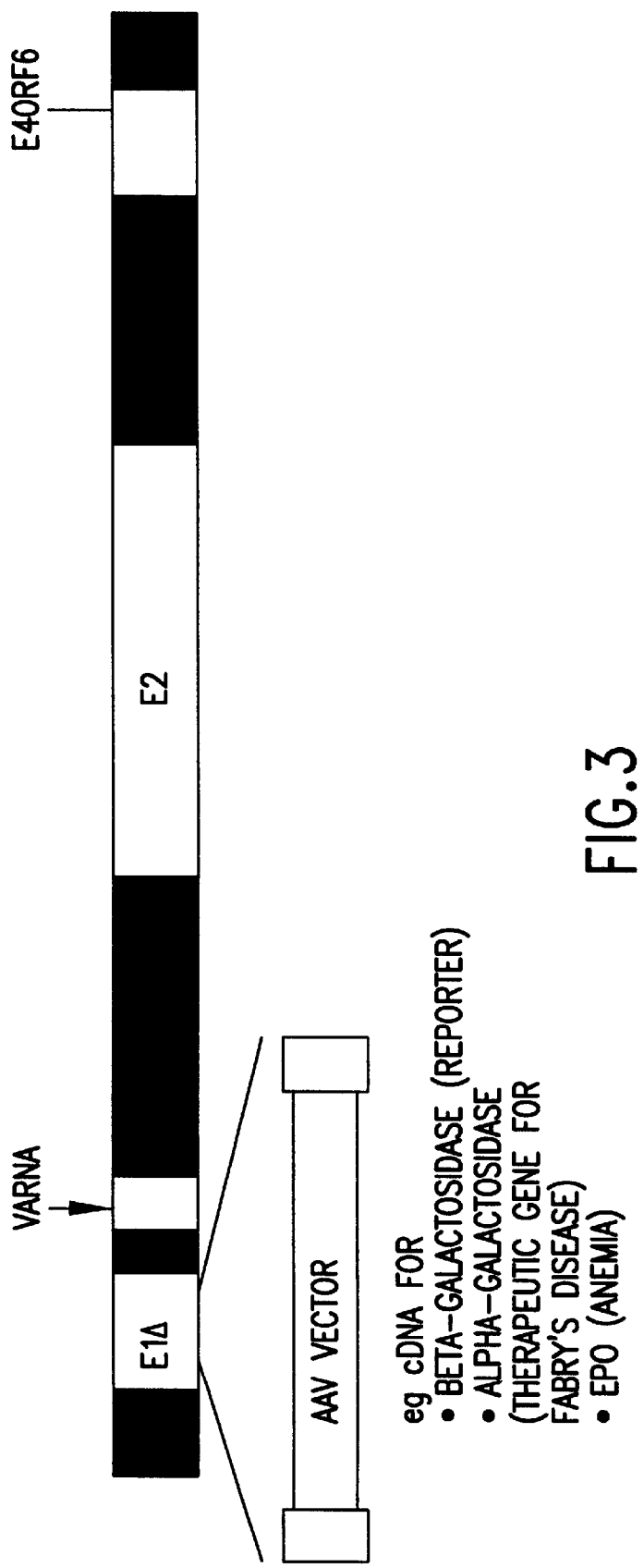
FIG. 3 show s schematic diagram of a hybrid adenovirus/rAAV helper adenovirus.

A representative adenovirus/rAAV hybrid vector of the invention is shown in FIG. 3, from which several advantageous features of such a design may be seen. This vector contains various adenovirus genomic regions necessary for rAAV production, including E1A, E1B, E2A, VA RNA and E4ORF6. Other embodiments of the adenovirus genome are possible, e.g., the inclusion of the wild-type E4 region in the vector, rather than just ORF6. The rAAV vector genome comprising a transgene operably linked to expression control sequences is preferably inserted into a deletion in the E3 region of the adenovirus genome. The advantage of the hybrid vector is that it is replication competent, and can be manufactured at commercial scale by growth on A549 or HeLa cells, for example. Furthermore, the hybrid vector can also undergo replication in the monkey producer cells of the system, providing additional copies of the rAAV vector genome contained in the vector. Where a hybrid vector contains only E4 ORF6, such a vector exhibits reduced synthesis of the adenovirus fiber protein, thereby further limiting production of virus progeny (Armentano et al., Hum. Gene Ther. 6:1343–1353, 1995). This hybrid vector can be used to deliver a variety of rAAV genomic designs, since, in this embodiment, the adenovirus contains a deletion in its E3 region from nucleotides 27,971 to 30,937 into which a vector genome comprising a transgene and associated control sequences can be inserted.

A further preferred embodiment of the invention is a producer system comprising a monkey cell line comprising AAV helper genes and an adenovirus/rAAV hybrid vector. This combination is advantageous in that it requires only the infection of the producer cell by the hybrid vector in order to initiate rAAV production. A further advantage of this system is that the AAV genes in the producer cell are transcriptionally silent until infection of the cell by the helper adenovirus which causes transactivation of the AAV virus promoter, leading to AAV gene expression.

Preferably, the AAV rep and cap genes provided by pIM45 or p5repΔCMVcap (Vincent et al., J. Virol. 71:1897–1905, 1997) are integrated into the producer cell genome and an rAAV vector genome comprising a trans gene operably linked to expression control sequences is cloned into the E3 region of an adenovirus genome comprising E1, E2, ΔE3 and E4 or an adenovirus genome comprising E1, E2, ΔE3 and E4ORF6 (Armentano et al., Hum. Gene Ther. 6:1343–1353, 1995). The producer cell line is an adapted non-human cell line according to the invention (e.g., a rodent cell line comprising a nucleic acid encoding CAR) or can be a monkey cell line, especially CV-1 cells.

In other aspects of the invention where monkey cell lines are used as producer cell lines, specific mutations can be introduced into the human adenovirus used to create the hybrid adenovirus/rAAV vector such that it displays a phenotype that allows for the manipulation of growth efficiency of the adenovirus. For example, viruses containing mutations that confer temperature-sensitive production of the fiber protein can be used to produce rAAV at the restrictive temperature, such that the formation of adenovirus progeny is depressed, thereby leading to an enriched preparation of the rAAV vector stock. With the knowledge of the molecular and genetic maps of adenovirus serotypes 2 and 5, the skilled artisan can introduce such mutations into an adenovirus/rAAV hybrid 30 vector by standard cloning techniques, e.g. by site-directed mutagenesis. In a preferred embodiment, the adenovirus used to create the hybrid vector is H5ts142 or is an adenovirus engineered to contain a specific mutation that confers a similar phenotype (Chee-Sheung et al., J. Virol. 42:932–950, 1982).

Other hybrid vectors useful in monkey cell line production systems include, inter alia, a hybrid adenovirus/rAAV vector which is derived from adenoviral mutant Adts400 containing a mutation in the adenovirus DNA binding protein that restricts the formation of virus progeny at the nonpermissive temperature in CV-1 or HeLa cells (Rice et al., J. Virol. 49:35–49, 1984). Other temperature-sensitive adenovirus mutants which depress viral yield useful in the present invention include, inter alia, a ts mutation in the fiber gene of adenovirus 5 (Chee-Sheung et al., J. Virol. 42:932–950, 1982; ts mutations in a non-structural protein, p100, with the phenotype of reduced capsid assembly (Carstens et al., J. Gen. Virol. 37:453–474, 1997; Oosterom-Dragon et al., J. Virol. 40:491–500, 1981) and ts mutations in the IIIa gene of adenovirus 2, with the phenotype of defective late gene expression and detective virus packaging (Chroboczek et al., Gene 49:157–160, 1986). Where the hybrid vector is created from an adenovirus having a temperature-sensitive mutation, the entire rAAV production process is carried out at a nonpermissive temperature of 39.5° C.

The nucleic acid comprising the rAAV vector genome used in the production of rAAV vectors preferably contain the cis-acting invented terminal repeat elements (ITRs) and one or more nucleic acids of interest (transgenes) operably linked to expression control sequences. Such expression control sequence include promoters, enhancers, and polyadenylation elements. Viral or non-viral promoters can be operably linked to a transgene in a rAAV vector, including the CMV promoter or functional variants thereof, or a PGK promoter, or any other promoters known to be useful for the expression of a transgene. The expression control sequences may result in cell or tissue-specific expression or may be inducible by exogenous agents or stimuli, e.g., RU 486 or other small molecules capable of inducing gene expression.

The rAAV vectors comprise a transgene. A transgene is identified as a nucleic acid which is exogenously provided to a cell by any method of gene transfer. Transgenes which can be delivered and expressed from an rAAV vector of the invention include, but are not limited to, those encoding enzymes, blood derivatives, hormones, lymphokines such as the interleukins and interferons, coagulants, growth factors, neurotransmitters, tumor suppressors, apoliproteins, antigens, and antibodies, and other biologically active proteins. Specific transgenes which may be encoded by the rAAV vectors include, but are not limited to, nucleic acids coding for cystic fibrosis transmembrane conductance regulator (CFTR), erythropoietin (EPO), β-glucocerebrosidase, α-galactosidase, tumor necrosis factor, p53, p21, factor VIII, factor IX, herpes simplex thymidine kinase and gancyclovir, retinoblastoma (Rb), and adenosine deaminase (ADA). Transgenes encoding antisense molecules or ribozymes are also within the scope of the invention. The rAAV vectors so constructed can be used for gene transfer of a transgene because they are capable of entering target cells, integrating their nucleic acids into the target cell genome, and stably expressing the transgene in such cells.

In a preferred embodiment of the invention where the nucleic acid of a rAAV vector is stably integrated into a cell line of the invention, such integration can be accomplished following the introduction of such sequences on a plasmid by, for example, transfection, lipofection or electroporation. Use of a plasmid containing a rAAV genome and a nucleic acid encoding a selectable marker allows for the identification of cells with stable integration of the rAAV genome. With adequate provision of AAV helper proteins and upon infection by a helper virus, such nucleic acid can be rescued from the cellular genome for replication and packaging into rAAV vector particles.

In one embodiment of the invention, the plasmid used to deliver an rAAV vector genome (t transgene) into a cell line for stable integration therein is pNTC3CMVβgal, a plasmid constructed by standard recombinant techniques in which a marker transgene (lacZ encoding β-galactosidase) operably linked to a CMV promoter is flanked by AAV ITR sequences. This plasmid allows for quantitation of vector production in a cell line of the invention by hybridization to complementary nucleotide sequences in the rAAV vector genome or by detection of the produced marker protein (β-galactosidase) using X-gal staining.

In addition to the rAAV vector nucleic acid provided to a producer cell line of the invention by exogenous delivery or by stable integration therein, production of rAAV vectors requires the provision of AAV helper proteins that are required in trans for vector production. The AAV rep and cap genes can be supplied to a producer cell line in a plasmid or in a non-AAV helper virus. Helper plasmids contain the AAV rep and cap genes, operably linked to one or more regulatory elements which allow expression from the genes to generate the rep and cap proteins required for the production of rAAV vectors. The AAV genes can be expressed from their native viral promoters, or can be operably linked to heterologous promoters which increase expression, including, but not limited to, the CMV promoter or functional variants thereof. The rep and cap genes can be expressed from separate regulatory elements which allow for selective optimization of the required levels of expression of the proteins. Where the rep gene is under the control of its native promoter, stable integration of this gene into a producer cell line reduces potential cytoxicity from constitutive production of the rep protein because the p5 promoter requires the adenovirus E1A protein for tranactivation, and this will occur only upon infection by the helper adenovirus in the initiation of a cycle of rAAV vector production.

Where AAV helper genes and their operably linked regulatory elements are stably integrated into a cell line of the invention, such integration of the AAV helper genes can be accomplished by introduction of a plasmid comprising such genes into a cell line of the invention, using transfection or other methods of nucleic acid transfer known to those skilled in the art. The AAV helper plasmid preferably contains a selectable marker or reporter gene, which, upon expression, allows for identification of cells which contain the helper genes integrated into the genome of the producer cell line. Helper plasmids used for the creation of producer cell lines with stably integrated AAV helper genes are first be tested for their ability to support rAAV production in transient transfection experiments.

A stable cell line for rAAV vector production has numerous advantages over the transient transfection method. First, the transfection methods are difficult to scale up to the amounts required for commercial manufacturing of rAAV vectors. Second, rodent and monkey cell lines, when used to produce rAAV vectors, have a low transfection efficiency. Thus, the ratio of rAAV vector to helper adenovirus using stable cell lines is far greater than that obtained in the transient method.

Preferred AAV helper plasmids which are used in any producer cell line of the invention to provide the AAV helper proteins include, inter alia, pIM45 (McCarty, D. M. et al., J. Virol. 65:2936–2945, 1991), containing the AAV rep and cap genes under control of the native p5 and p40 promoters, and p5repΔCMVcap (in Vincent et al., J. Virol. 71:1897–1905, 1997). Preferably, p5repΔCMVcap is used to establish the producer cell line. In plasmid p5repΔCMVcap, the rep gene is under the control of the native p5 promoter, while the cap gene is operably linked to the cytomegalovirus (CMV) promoter for high level expression of the structural proteins.

Where a rAAV vector genome and AAV helper genes are provided together on one plasmid to a producer cell line, the plasmid is constructed to contain at least the minimal sequences for the rAAV vector (ITRs flanking a transgene of interest) and for the AAV helper (rep and cap genes under the control of desired regulatory elements), and further contains a selectable marker which allows the identification of stably transfected cells. An example of such a plasmid, pVH-16+neo (FIG. 1) is used to transfect a producer cell line. The pVH-16+neo plasmid contains a CMV-lacZ expression cassette flanked by the AAV inverted terminal repeats (the rAAV vector), and the AAV helper genes, including the cap gene operably linked to a CMV promoter and the rep gene operably linked to the p5 promoter. It further comprises the neomycin (neo) resistance gene operably linked to the SV40 promoter. The producer cell line is adapted to allow the binding and entry of a non-AAV helper virus, (e.g., human adenovirus), which cannot generate a productive infection, but which provides the helper proteins required in trans. Alternatively, the producer cell line is natively susceptible to entry by such helper virus, but cannot support a productive infection. Upon stable integration of the rAAV vector and AAV helper genes, carried by using pVH-16+neo into the producer cell genome, the producer cell line simply requires infection by the non-AAV helper virus in order for rAAV production to occur. The advantage of this production system is that it only requires infection by helper adenovirus to initiate rAAV production.

The invention is also directed to methods for the production of rAAV vectors using the producer cell lines of the invention. In one preferred method, a producer cell line comprises and expresses a nucleic acid encoding a receptor for a non-AAV helper virus, e.g. adenovirus, which can bind to and enter the cells but cannot generate a productive infection. The producer cell line also comprises a rAAV vector genome and AAV helper genes stably integrated into its genome. Production of rAAV vectors requires, therefore, only the infection of the producer cell line with the helper virus. Upon such infection, the rAAV vector genome is excised, replicated and encapsidated into viral particles which can be used in gene transfer. Preferably, such producer cells are infected with a non-AAV helper virus at a multiplicity of infection (MOI) from 5 to 100.

Recovery of rAAV vectors is performed using cell lysates derived from the producer cells of the invention. The lysate can be fractionated using standard density gradient centrifugation, e.g., a CsCl gradient. Such gradient purification removes any contaminating non-AAV helper virus.

Alternatively, any non-AAV helper virus can be removed by heat inactivation of the cell lysate. However, the producer cell lines, helper viruses, and methods of the invention result in the production of rAAV vector stocks that are essentially free of non-AAV helper virus.

Alternatively, rAAV purification can be performed using chromatographic techniques, e.g., as set forth in PCT Publication No. WO97/08298, incorporated herein by reference.

Quantitation of rAAV vectors using the cell lines and methods of the invention can be measured by determination of virus yield. To determine virus yield, a standard AAV infectious center assay can be used to assay for production of infectious progeny. The vector sample to be tested is used to infect 293 cells, for example, that are also infected with helper adenovirus and wild-type helper AAV. Following a period of incubation to allow for vector replication, the cells are recovered and lysed on filters, then hybridized to a nucleic acid that is known to hybridize to vector DNA. Positive hybridization identifies an infectious center. The titer of the starting material is determined by multiplying the number of infectious centers by any dilution used in the preparation of test samples. Where the rAAV vector in production contains a reporter gene as the transgene, alternative methods for determining the rAAV vector titer can be used. For example, if the lacZ transgene is used, the infected cells can be stained for the production of the gene product, β-galactosidase, using X-gal staining. Titer is determined, for example, by counting the blue-stained cells in a plate well. Other methods for determining rAAV vector production include electron microscopy of samples for viable capsids or immunofluorescence of infected cells using monoclonal antibodies against the AAV capsid proteins.

The titer of any contaminating helper virus can be obtained by an assay appropriate to the source of the helper virus; e.g., where adenovirus is used as a helper virus, any contamination can be quantitated by standard techniques, such as plaque formation in 293 or HeLa cells.

The producer cell lines, helper adenoviruses and methods of the invention generate rAAV vector stocks that are essentially free of non-AAV helper virus; preferably, such helper viruses are detected at less than one helper virus per $10^{10}$ rAAV vector particles. The reagents and methods of the invention have utility for the production of purified stocks of rAAV vectors which can be used for gene transfer in a wide variety of applications.

The practice of the invention employs, unless otherwise indicated, conventional techniques of protein chemistry, molecular virology, microbiology, recombinant DNA technology, and pharmacology, which are within the skill of the art. Such techniques are explained fully in the literature. See, e.g., *Current Protocols in Molecular Biology*, Ausubel et al., eds., John Wiley & Sons, Inc., New York, 1995, and Remington's Pharmaceutical Sciences, 17th ed., Mack Publishing Co., Easton, Pa., 1985.

The invention is further illustrated by the following specific examples which are not intended in any way to limit the scope of the invention.

EXAMPLE 1

Transient Transfection Packaging of AAV in Rodent Cells Expressing a Nucleic Acid Encoding CAR To confirm the activity of the helper plasmid constructs to be used in constructing stable cell lines, a transient transfection packaging experiment was carried out on 293 cells (a positive control), mouse A9-T14 cells (single copy of CAR gene), mouse A9-2498.1 and A9-2498.6 cells (each with multiple copies of a BAC clone encoding the CAR gene), and mouse A9-Mam1R+ or A9-Mam2R+ cells (lacking the CAR gene). The AAV vector plasmid was pNTC3CMVβgal (1.5 ug/$10^6$ cells), the AAV helper plasmid was p5repΔCMVcap (15 ug/$10^6$ cells) and wild-type helper adenovirus was used at 5.6 IU/$10^9$ cells. The cells are infected with adenovirus one hour before transfection of the plasmids by calcium-phosphate-mediated transfection, which is applied to the cells for an additional 4 hours.

The transfected/infected cells were incubated for 2 days at 37° C. After incubation, the cells were harvested and then lysed by three (3) freezing and thawing cycles in the presence of benzonase (American International Chemical). 1% deoxycholate and 0.25% trypsin was then added to the lysate, followed by incubation for 30 min at 37° C. The cell lysate (2 roller bottles/gradient) was then applied to a CsCl step gradient (1.5 g/ml–1.36 g/ml) in a SW28 rotor and centrifuged at 26K for 6 hours at 4° C. Fractions were obtained and then further purified on two equilibrium gradients, using a NVT65 rotor, and centrifuged at 60K for 20 hours at 4° C. Fractions from the equilibrium gradients were screened on a refractometer and pooled. Pooled fractions were dialyzed in PBS with 1% sucrose 3 times for 2 hours at 4° C.

The efficiency of a helper plasmid as a source of proteins required in trans was determined from the yield of AAV vector stock. To determine virus yield, an AAV infectious center assay was used, which shows whether infectious AAV progeny are produced in the production protocol. The recombinant AAV vectors were recovered after production using the purification protocol described above.

The assay was performed with 293 cells that were plated on day one at a density of $1 \times 10^5$ cells per well in 0.1 ml/well in DME medium supplemented with 10% FBS, penicillin/streptomycin, and glutamine. After about 24 hours, the cells were infected with adenovirus at an MOI of 20 and with wild-type AAV at an MOI of 2. The viruses were suspended in the same medium and 0.1 ml was added to each well to initiate infection. The AAV vector samples were added to the well (25–100 microliters of lysate or dilutions) and the plates were incubated for 24–30 hours at 37° C. On the day after infection, the medium was carefully removed from the cells. Cells were then fixed and subjected to X-gal straining and the number of blue cells were recorded.

The results shown in Table 1 demonstrate that mouse cells expressing a nucleic acid encoding CAR function as an efficient producer cell for rAAV vector when provided with the appropriate AAV and adenovirus helper functions. Importantly, from the A9-2498.1 and A9-2498.6 cells, the ratio of AAV vector yield to contaminating Ad virus yield was 280, while in 293 cells the ratio was approximately 0.03. This increase in the ratio of AAV vector to adenovirus greatly simplifies the subsequent purification of AAV vector from contaminating adenovirus.

TABLE 1

| Cell line | Titer |
|---|---|
| Ad titer | |
| (+) control | $3.4 \times 10^{10}$ |
| T14 (single copy of CAR) | $5.3 \times 10^6$ |
| 2498.1 (BAC clone of CAR-multiple copies) | $5.6 \times 10^6$ |
| 2498.6 (BAC clone of CAR-multiple copies) | $7.9 \times 10^5$ |

TABLE 1-continued

| Cell line | Titer |
|---|---|
| Mam1R+ (empty vector) | $3.1 \times 10^6$ |
| Mam2R+ (empty vector) | $3.8 \times 10^6$ |
| AAV Titer | |
| (+) control | $1.0 \times 10^9$ |
| T14 | $3.1 \times 10^7$ |
| 2498.1 | $2.7 \times 10^8$ |
| 2498.6 | $1.1 \times 10^8$ |
| Mam1R+ | $3.0 \times 10^6$ |
| Mam2R+ | $2.8 \times 10^6$ |

EXAMPLE 2

Establishment of Stable rAAV Producer Cell Lines

To make a stable rodent cell line for rAAV production, the plasmids pIM45/neo or p5repdeltaCMVcap/neo which provide AAV helper functions and a selectable marker for clone selection are introduced into A9-2498.1 and A9-2498.6 cells. Cells are plated out at $2.5 \times 10^6$ cell per 10 cm dish. The next day the plasmid construct is introduced into cells using calcium-phosphate-mediated transfection. The following day, each dish is split into 5 10-cm dishes and on the subsequent day, selective media containing G418 (between 100 to 500 µg/ml) is applied. Clones appear from 10 to 14 days later, when they are picked into 96 well dishes and allowed to grow to near confluency.

Cells are split into a 96 well plate for maintaining the clones and another 96 well plate for screening for rAAV production. For screening, the cells are transfected with pNTC3CMVβgal and infected with adenovirus at an MOI of 20. 48 hours later the plate is freeze-thawed 4 times to release rAAV vectors. Production of rAAV vector is measured by determining the titer of the lysate as described above in Example 1.

EXAMPLE 3

A Replication-defective Ad/AAV Hybrid for AAV Manufacturing

Using standard molecular methods, the rAAV vector genome is inserted into the E1 region of Ad2, between nucleotide positions 358 and 3328. To ensure adequate space for the ArAV genome, the E4 region of the vector is modified by deletion of all E4 sequences (deletion between nucleotides 32802195 to 35577) and insertion of the ORF6 coding sequence (nucleotides 33195 to 34077) (Armentano et al 1995, Human Gene Therapy, vol 6, 1343–1353). The Ad/rAAV vector is otherwise wild-type in sequence. The AAV vector genome consists of the AAV left and right ITRs (145 to 173 base pairs in length), the CMV promoter operably linked to the transgene (e.g., *E. coli* beta-galactosidase for reporter applications, EPO transgene) (FIG. 3). Packaging of rAAV vectors is accomplished by infection of the stable producer cell line of Example 2 with the replication-defective Ad/AAV hybrid and a wild-type Ad virus (to provide E1 functions). Between 48 and 96 hours post infection, cells are lysed to release packaged AAV vector and purified away from contaminating products such as the small amounts of Ad virus produced and cellular proteins.

EXAMPLE 4

Construction of a Replication-competent Ad/AAV Hybrid for AAV Manufacturing

Figure 4:
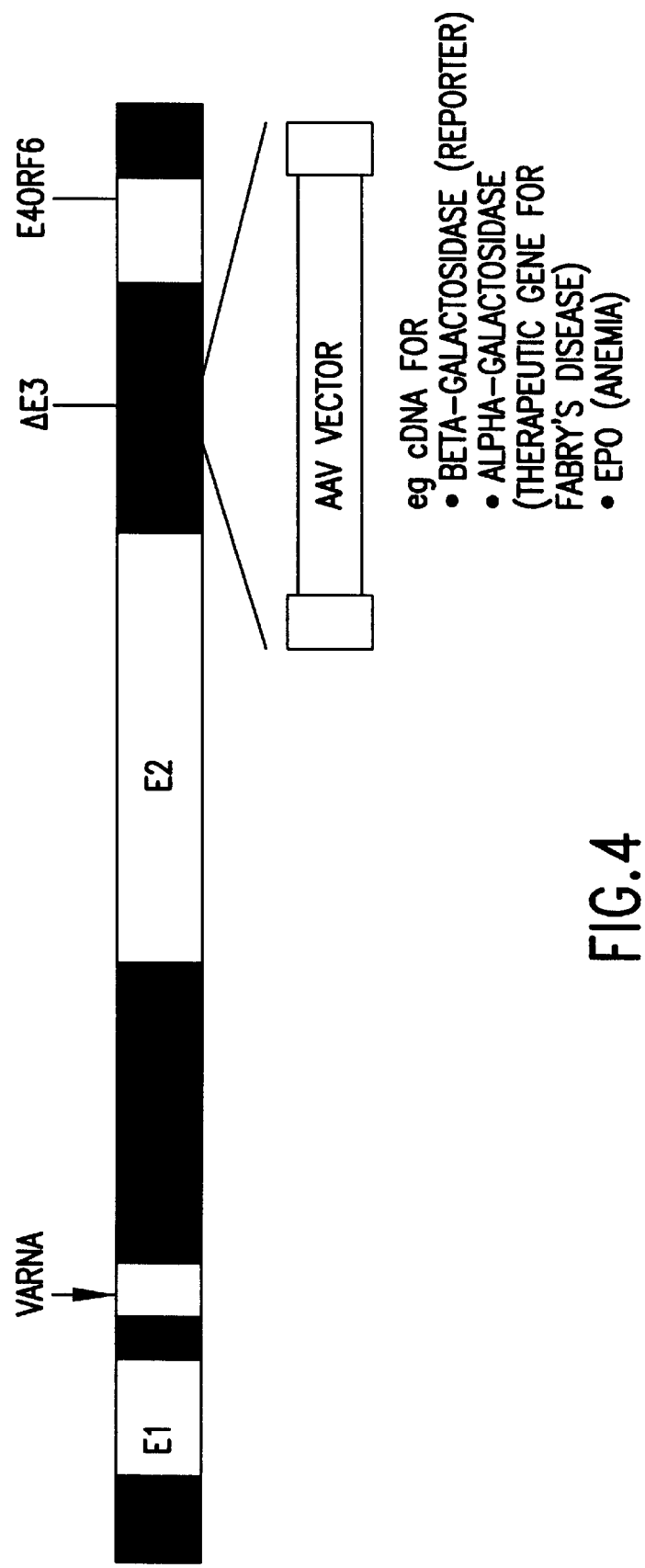
FIG. 4 shows a schematic diagram of a hybrid adenovirus/rAAV helper adenovirus.

Using standard molecular methods, the AAV vector genome is inserted into the E3 region of Ad2, between nucleotide positions 27,971 and 30,937. To ensure adequate space for the AAV genome, the E4 region of the vector is modified by deletion of all E4 sequences (deletion between nucleotides 32802 and 35577) and insertion of the ORF6 coding sequence (nucleotides 33195 to 34077) (Armentano et al 1995, Human Gene Therapy, vol 6, 1343–1353). The Ad/AAV vector is otherwise wild-type in sequence. The AAV vector genome consists of the AAV left and right ITRs (145 to 173 base pairs in length), the CMV promoter operably linked to the transgene (e.g., *E. coli* beta-galactosidase for reporter applications, EPO transgene) (FIG. 4). Packaging of AAV vector is accomplished by infection of the stable producer cell line of Example 2 with the replication-competent Ad/AAV hybrid. Between 48 and 96 hours post infection, cells are lysed to release packaged AAV vector and purified away from contaminating products such as the small amounts of Ad virus produced and cellular proteins.

What is claimed is:

1. A method for rAAV vector production comprising:
   a) transfecting a non-human cell line with a nucleic acid encoding a cocksackie and adenovirus receptor (CAR);
   b) transfecting said cell line with a helper human adenovirus that is unable to produce a productive infection in the cell line;
   c) transfecting said cell line with an rAAV genome, wherein said rAAV genome comprises AAV ITR sequences and a transgene operably linked to expression control sequences;
   d) further transfecting said cell line with a nucleic acid encoding AAV rep and cap proteins; and
   e) isolating the rAAV vectors produced in said cell line.

2. The method of claim 1, wherein the non-human cell line is a CV-1 cell line.

3. The method of claim 2, in which the helper adenovirus is a temperature-sensitive mutant adenovirus.

4. The method of claim 1, in which the helper adenovirus is a temperature-sensitive mutant adenovirus.

5. The method of claim 1 wherein said non-human cell line is selected from the group consisting of mouse, rat, hamster and monkey.

6. A method for rAAV vector production, comprising:
   a) transfecting a monkey cell line with a nucleic acid encoding a cocksackie and adenovirus receptor (CAR);
   b) transfecting said cell line with a helper human adenovirus that is unable to produce a production infection in the cell line;
   c) transfecting said cell line with a stably integrated rAAV genome, wherein said rAAV genome comprises AAV ITR sequences and a transgene operably linked to expression control sequences;
   d) transfecting said cell line with a nucleic acid encoding AAV rep and cap proteins; and
   e) isolating the rAAV vectors produced in said cell line.

7. The method of claim 6, in which the helper adenovirus is a temperature-sensitive mutant adenovirus.

8. The method of claim 6 wherein said monkey cell line is selected from the group consisting of CV-1, CV-C, Vero, and BSC-1.

9. The method of claim 1 or 6 wherein said helper human adenovirus is derived from adenoviral serotype selected from the group consisting of type 2 and type 5.

10. The method of claim 1 or 6, wherein said transgene is a nucleic acid selected from the group consisting of the cystic fibrosis transmembrane conductance regulator (CFTR), erythropoietin (EPO), α-galactosidase, β-glucocerebrosidase, tumor necrosis factor, p53, p21, factor VIII, factor IX, herpes simplex thymidine kinase, gancyclovir, retinoblastoma (Rb), and adenosine deaminase (ADA).

11. A method for rAAV vector production, comprising:
   a) transfecting a monkey cell line comprising a stably integrated nucleic acid encoding a cocksackie adenovirus receptor (CAR) with a helper human adenovirus that is unable to produce an infection in the cell line, wherein said helper human virus is temperature sensitive;
   b) transfecting said monkey cell line with an rAAV vector plasmid, wherein said rAAV vector plasmid comprises AAV ITR sequences and a transgene operably linked to an expression control sequence;
   c) transfecting said monkey cell line with a helper plasmid comprising AAV rep and cap proteins; and
   d) isolating the rAAV vectors produced in said monkey cell line.

12. The method of claim 11 wherein said monkey cell line is selected from the group consisting of CV-1, CV-C, Vero, and BSC-1.

13. A method for rAAV vector production, comprising:
   a) transfecting a mouse cell line comprising a stably integrated nucleic acid encoding a cocksackie and adenovirus receptor (CAR) with a helper human adenovirus that is unable to produce an infection in the cell line, wherein said helper human virus is temperature sensitive;
   b) transfecting said mouse cell line with an rAAV vector plasmid, wherein said rAAV vector plasmid comprises AAV ITR sequences and a transgene operably linked to an expression control sequence;
   c) transfecting said mouse cell line with a helper plasmid comprising AAV rep and cap proteins; and
   d) isolating the rAAV vectors produced in said mouse cell line.

14. The method of claim 13, wherein said mouse cell line is selected from the group consisting of mouse A9 and mouse L929.

* * * * *